US006895275B2

(12) United States Patent
Markowitz et al.

(10) Patent No.: US 6,895,275 B2
(45) Date of Patent: May 17, 2005

(54) METHODS AND APPARATUS FOR DETECTION AND TREATMENT OF SYNCOPE

(75) Inventors: Harold Toby Markowitz, Roseville, MN (US); Mark K. Erickson, Brooklyn Park, MN (US); Alan V. Sahakian, Northbrook, IL (US); Andreas Schuler, Pewaukee, WI (US)

(73) Assignee: Medtronic, Inc., Minneapolis, MN (US)

( * ) Notice: Subject to any disclaimer, the term of this patent is extended or adjusted under 35 U.S.C. 154(b) by 568 days.

(21) Appl. No.: 10/053,762

(22) Filed: Jan. 22, 2002

(65) Prior Publication Data

US 2003/0139780 A1 Jul. 24, 2003

(51) Int. Cl.[7] .............................................. A61N 1/362
(52) U.S. Cl. ....................................................... 607/18
(58) Field of Search ....................................... 607/9–29

(56) References Cited

U.S. PATENT DOCUMENTS

| | | | |
|---|---|---|---|
| 5,284,491 A | 2/1994 | Sutton et al. .................. | 607/17 |
| 5,464,434 A | 11/1995 | Alt .................................. | 607/6 |
| 5,501,701 A | 3/1996 | Markowitz et al. ............. | 607/9 |
| 5,540,728 A | 7/1996 | Shelton et al. ................. | 607/23 |
| 5,676,686 A | 10/1997 | Jensen et al. .................. | 607/9 |
| 5,919,210 A | 7/1999 | Lurie et al. ..................... | 607/3 |
| 6,049,735 A | 4/2000 | Hartley et al. .................. | 607/9 |
| 2002/0004672 A1 | 1/2002 | Florio et al. | |

OTHER PUBLICATIONS

Benditt, David G. et al., "Rate–Drop Response" Cardiac Pacing for Vasovagal Syncope, *Journal of Interventional Cardiac Electrophysiology*, vol. 3, p. 27–33 (1999).

Benditt, David G. et al., "Heart Rate and Blood Pressure Control in Vasovagal Syncope," *Journal of Interventional Cardiac Electrophysiology*, vol. 2, p. 25–32 (1998).

Benditt, David G. et al., "A Synopsis: Neurocardiogenic Syncope, An International Symposium, 1996," *PACE*, vol. 20, p. 851–860 (Mar. 1997, Part II).

Furlan, Raffaello et al., "Cardiac Autonomic Patterns Preceding Occasional Vasovagal Reactions in Healthy Humans," *Circulation*, vol. 98, p. 1756–61 (Oct. 27, 1998).

Kurbaan, Arvinder S. et al., "Respiratory Changes in Vasovagal Syncope," *J Cardiovasc Electrophysiol*, vol. 11, p. 607–11 (Jun. 2000).

Oh, Jeong H. et al., "Do Symptoms Predict Cardiac Arrhythmias and Mortality in Patients With Syncope?" *Arch Intern Med*, vol. 159, p. 375–80 (Feb. 22, 1999).

*Primary Examiner*—Scott M. Getzow
(74) *Attorney, Agent, or Firm*—Girma Wolde-Michael; Daniel G. Chapik (57) ABSTRACT

The present invention relates to methods and apparatus for detection and treatment of syncope in an implantable medical device, and particularly to detection of syncope as a function of a predetermined increase in one or more respiration parameter and drop in heart rate and optionally delivering a pacing therapy in response thereto. The onset of a syncopal episode is declared when the patient's respiration rate and/or tidal volume and/or minute ventilation increases by a predetermined increment or threshold and a heart rate drops below a threshold heart rate drop. The threshold heart rate drop is preferably established as a function of the change in the respiration parameter.

20 Claims, 6 Drawing Sheets

METHODS AND APPARATUS FOR DETECTION AND TREATMENT OF SYNCOPE

FIELD OF THE INVENTION

The present invention relates to methods and apparatus for detection and treatment of syncope in an implantable medical device, and particularly to detection of syncope as a function of a predetermined change in respiration and heart rate and optionally delivering a pacing therapy in response thereto.

BACKGROUND OF THE INVENTION

Vasovagal syncope is a condition marked by a sudden drop in heart rate and blood pressure, resulting in fainting. It is not only unpleasant for a patient, but potentially dangerous, as fainting may lead to injuries from falls and increase the risk of motor vehicle accidents. The condition affects many thousands of patients, and particularly, the elderly. Many such patients present at emergency rooms with a wide variety of injuries due to falling.

A cardiac pacing system is disclosed in U.S. Pat. No. 5,284,491 that is specifically adapted to treat patients suffering from vasovagal syncope. In particular, the pacemaker detects when the patient's heart rate drops below a lower "hysteresis" rate and determines whether the average rate of decrease in the patient's heart rate, over a defined number of heartbeats or a defined time interval prior to reaching the "hysteresis" rate, is greater than a preset value. If so, the pacing rate is set equal to the "hysteresis" rate and thereafter increased to an "intermediate" rate substantially higher than the "hysteresis" rate. The pacing rate remains at the "intermediate" rate for a preset time period and thereafter gradually declines to a lower pacing rate.

Commonly assigned U.S. Pat. No. 5,501,701 discloses an improved pacing system for the treatment of patients with vasovagal syncope that differs from the prior pacing system disclosed in the Sutton, '491 patent in that the methods of detection of an episode of vasovagal syncope and the intervention therapy delivered in response are refined. A persistent rate above a first threshold rate is required to initiate the rate drop detection function rather than detecting a rapid rate drop thereby preventing single rapid heartbeats from triggering detection of a rapid rate drop. A persistent or stable heart rate (e.g., x of y beats less than the drop rate) is required following detection of a rapid rate drop from above the first threshold rate to a rate below a second threshold rate or "drop rate" before the pacing rate is changed. Criteria for exiting the intervention therapy and for exiting the detection process due to sensed spontaneous depolarizations are also provided.

Commonly assigned U.S. Pat. Nos. 5,540,728 and 5,676, 686 disclose further improved pacing systems for the treatment of patients with vasovagal syncope wherein the detection of rate drop employs a process for defining the highest persistent rate over a period of time preceding the fall of the heart rate below the drop rate. The heart rate is monitored over a series of time intervals, with the fastest two-beat sequence in each time interval identified. The rate of the slower of the two beats in the identified sequence is stored as a "top rate", and the fastest of the "top rates" is identified as the highest persistent rate. The measured rate drop is then taken as the difference between the fastest such "top rate" and the heart rate following a drop below the drop rate. This process prevents short intervals as might result from premature depolarizations of the atrium or ventricle from erroneously triggering pacing at an increased rate.

In a further preferred embodiment, an alternative method of detecting vasovagal syncope and triggering an increased pacing rate is provided. The pacemaker in this embodiment keeps count of successive paced beats, and triggers an increased pacing rate in response to an extended series of paced beats at the base pacing rate.

Moreover, the vasovagal syncope detection function can be disabled during a defined sleep period, so that normal rate drops associated with sleep do not result in inappropriate triggering of pacing at an increased rate that could unnecessarily disturb the patient's sleep.

Further U.S. Pat. No. 6,049,735 incorporates a detection algorithm in which a precipitous rate drop from a pre-existing average intrinsic heart rate value to a lower rate limit is sensed. If the patient is awake and the intrinsic rate remains below the lower rate limit for a predetermined number of beats or interval, the patient's heart is paced at a rate that is a programmed differential above the prior average intrinsic rate for a second programmed time interval. The pacing rate is then gradually decreased to the average heart rate existing prior to the sudden rate drop or to the lower rate limit.

The pacing system is preferably incorporated into a rate adaptive pacemaker having means for sensing a parameter proportional to hemodynamic demand of the patient along with provisions for the conventional lower rate limit and upper rate limit thresholds. A drop in heart rate from the computed average heart rate existing prior to the drop down to a preprogrammed lower sensor rate limit for a predetermined number of beats triggers delivery of pacing pulses at a predetermined differential rate in excess of the average heart rate value existing immediately prior to the drop in heart rate.

To avoid false positives, the implantable cardiac rhythm management device may also include a sensor for determining minute ventilation, allowing respiratory rate and tidal volume parameters to be derived. The therapy delivery means is not only responsive to the rate drop sensing means, but also to the respiratory parameters to inhibit application of therapy pacing pulses above the average heart rate when the respiratory parameters are below a prescribed threshold indicative of a patient during sleep.

An implantable drug infusion device is disclosed in U.S. Pat. No. 5,919,210 that detects and treats syncopal episodes by infusing a suitable drug, e.g. beta blockers, alone or in combination with drug therapies. An algorithm is disclosed for determining the presence of syncope based on physiological activity associated with the onset of a syncopal episode. The physiological activities detected and used by the device are selected from the group including changes in heart rate, heart rate variability, QT interval, PR interval, pressure, blood flow, vagal nerve activity, temperature, pH, AV conduction times, respiration rate, position, motion, and combinations thereof.

Use of certain of these "physiological activities" in an implantable medical device is also disclosed in U.S. Pat. No. 5,464,434 to provide a number of different controllable therapeutic functions including cardiac pacing, anti-tachycardia pacing, cardioversion, and defibrillation. The system of the '434 patent is directed toward detection of syncopal episodes associated with a malignant tachyarrhythmia warranting delivery of an anti-tachyarrhythmia therapy. Variations of one or more physiologic parameter of the patient indicative of the substantially instantaneous hemodynamic condition of the patient's heart are monitored. The physiologic parameter(s) sensed may be any of blood pressure, blood oxygen content, minute ventilation, central venous temperature, pulse rate, blood flow, physical activity, or other parameter for that purpose. The mean and standard deviation of a signal generated by the sensor over a predetermined time interval are calculated. The quotient of the standard deviation and the mean is also calculated in order to determine a sudden hemodynamic change such as a precipitous drop in cardiac output. An anti-tachyarrhythmia therapy, e.g. a defibrillating protocol, is then triggered.

Despite these improvements, there is a need to be able to detect the onset of a syncopal episode with greater speed and accuracy to provide a suitable pacing therapy to decrease the likelihood that the patient will faint.

SUMMARY OF THE INVENTION

The present invention is directed toward an improved monitor or pacing system or other therapy delivery system incorporated into an implantable medical device (IMD) for monitoring or treating patients with vasovagal syncope that determines the onset of a syncopal episode as a function of both a heart rate drop and an increase in a respiration parameter associated with syncopal episodes. In accordance with one aspect of the present invention, the onset of a syncopal episode is declared when the patient's respiration rate and/or tidal volume increases from a prior prevailing respiration rate and/or tidal volume by a predetermined threshold rate of change increment or absolute threshold value and a persistent or stable heart rate drops faster than a threshold rate of change increment or absolute threshold value. The correlation of a detected increase in the patient's respiration parameter along with a heart rate drop provides for faster and more robust detection of a syncopal episode.

When the present invention is incorporated into a implantable monitor, the respiration parameters and heart rate associated with a declared syncopal episode can directly uplink telemetry transmitted in real time automatically or when initiated by the patient or can be stored in IMD memory with a date and time stamp and, at a later time, uplink telemetry transmitted during a telemetry transmission to an external medical device to assess the patient's condition. Storage or transmission can be initiated when the patient's respiration rate and/or tidal volume increases from a prior prevailing respiration rate and/or tidal volume by a predetermined rate increment or to a threshold respiration rate and/or tidal volume and a persistent or stable heart rate drops below a threshold rate of change or just when the persistent or stable heart rate drops below a threshold rate of change.

These monitoring functions can be incorporated into an IMD having a pacing therapy delivery system as well as other therapies including drug delivery. When the present invention is incorporated into a pacing therapy delivery system, pacing following a prescribed syncope intervention pacing rate format is initiated for a prescribed syncope pacing intervention time when the syncope detection criteria are met.

Optionally, therapy delivery and/or data storage is initiated for a prescribed syncope pacing intervention time when a persistent or stable heart rate exhibits a separately defined heart rate drop, but the changes in the patient's respiration rate and/or tidal volume do not meet the respiration parameter criteria. In the pacing therapy context, a syncope episode pacing rate can be programmed to be delivered over the prescribed pacing intervention time. The separate rate drop criteria could represent a greater absolute drop or rate of change in prevailing heart rate than the rate drop criteria that must be satisfied when the respiration parameter criteria are met.

The combination of heart rate and respiration parameter criterion advantageously increases the confidence that a heart rate drop does represent a syncopal episode.

The detection of a syncopal episode is enhanced following the present invention. It is also not necessary to disable the syncope detection algorithm during a presumed nocturnal sleeping time. The combination of heart rate and respiration parameter criterion enables accurate detection of syncopal episodes that typically occur when a patient arises from sleeping during nocturnal hours.

The various aspects of the present invention can be practiced separately or in various combinations in therapy delivery or monitoring systems disclosed in further detail herein or in other combinations.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS

The present invention can be embodied in a cardiac monitor or pacing IMD or in other IMDs or EMDs. It will also be understood that the present invention may be implemented in ICDs and the like. For convenience, the example described hereafter comprises a pacing system IMD. Therefore, FIG. 1 generally shows a dual chamber, rate responsive pacemaker 10 capable of sensing demand for cardiac output and of pacing the atrium and ventricle of a type suitable for practicing the present invention implanted in a patient 12. The present invention can be practiced in simpler single chamber or more complex multi-chamber pacemakers with or without the ability to adjust pacing rate as a function of the patient's need for cardiac output.

Figure 1:
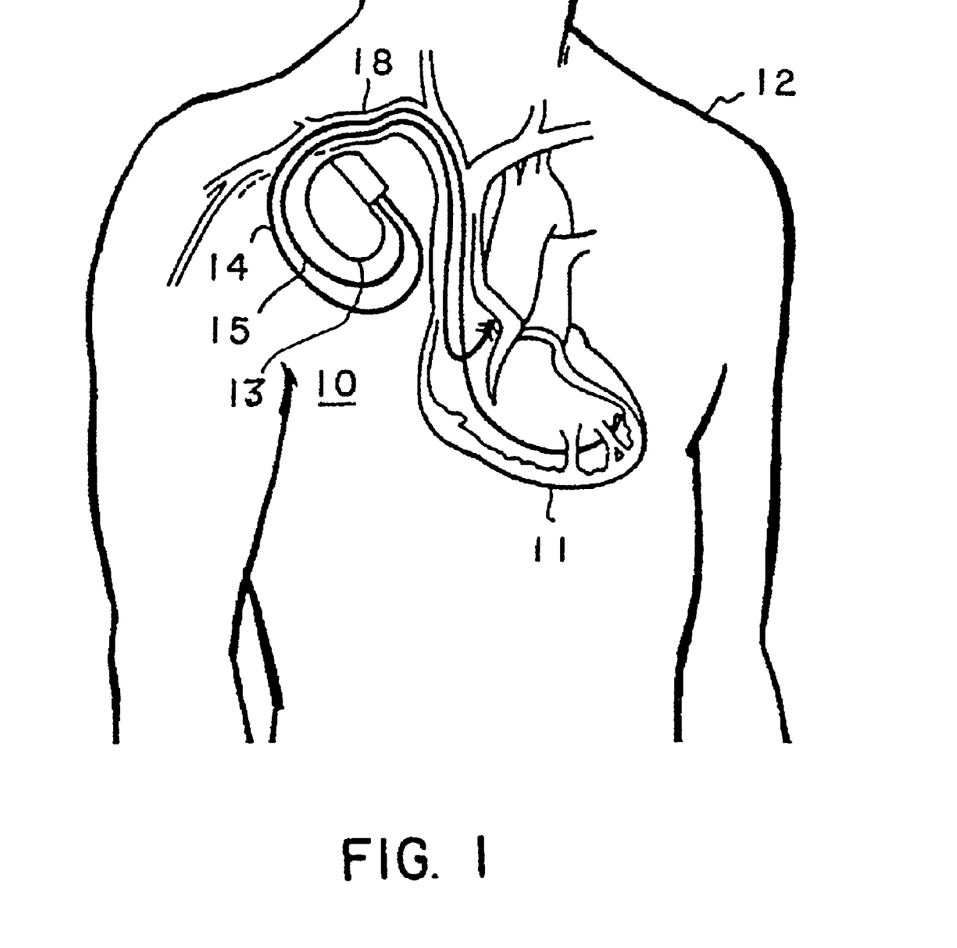
FIG. 1 schematically illustrates an IMD coupled with the heart of a patient through leads introduced into the right atrium and ventricles.

The illustrated pacemaker 10 comprises an implantable pulse generator (IPG) 13 coupled to leads 14 and 15 extending to the right ventricle and right atrium, respectively, of the patient's heart 11. Unipolar or bipolar pace/sense electrodes located in the distal segments of the leads 14 and 15 are employed to sense depolarizations of the heart, referred to informally herein as heart beats, and to deliver pacing pulses to the heart. Moreover, the respiration rate and tidal volume of the patient is derived by measuring impedance changes between selected pairs of pace/sense electrodes on the leads 14 and 15 and the IPG 13. The respiration rate and tidal volume can be derived in many ways other than impedance measurements.

Figure 2:
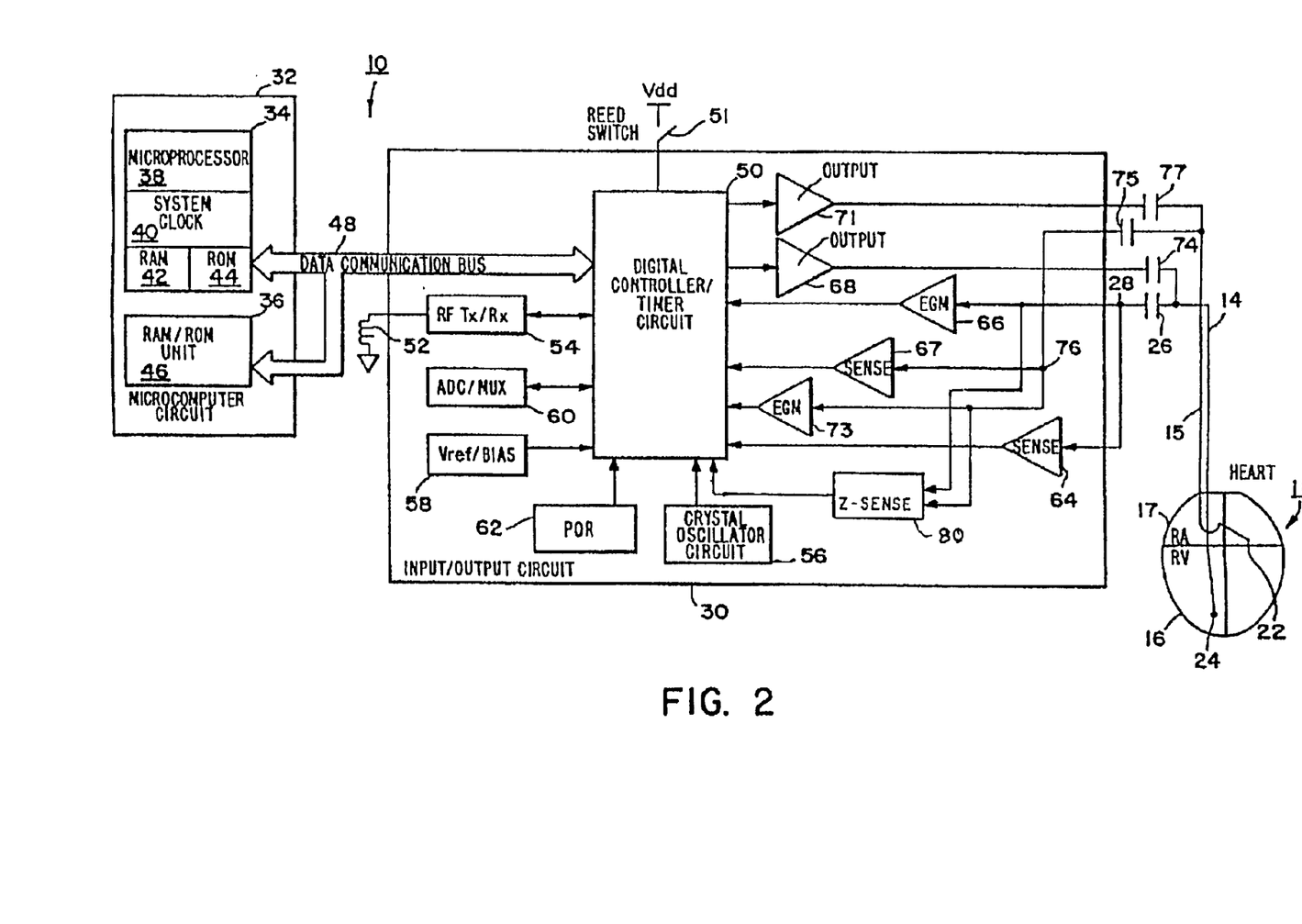
FIG. 2 is a schematic block diagram of an implantable pacing system in which the present invention may be practiced.

FIG. 2 is a block circuit diagram illustrating a multi-programmable, implantable, dual-chamber, bradycardia pacemaker 10 capable of carrying out the present invention comprising the IPG 13 and leads 14 and 15. The IPG operating system within IPG 13 includes a microprocessor-based microcomputer circuit 32 coupled through a data communications bus 48 with input/output circuit 30. It will be understood by those skilled in the art that the electrical components represented in FIG. 2 are powered by an appropriate implantable-grade battery power source (not shown). In a preferred embodiment of the present invention, pacemaker 10 is capable of operating in various non-rate-responsive modes that include DDD, DDI, WI, VOO, VVT, AAI and AOO, as well as corresponding rate-responsive modes of DDDR, DDIR, WIR, VOOR, VVTR, AAIR and AOOR. Furthermore, pacemaker 10 can be programmably configured to operate such that it varies its rate only in response to one selected sensor output, or in response to both sensor outputs, if desired.

Microcomputer circuit 32 comprises an on-board circuit 34 and an off-board circuit 36. On-board circuit 34 includes a microprocessor 38, a system clock 40, and on-board RAM 42 and ROM 44. Off-board circuit 36 includes an off-board RAM/ROM unit 46 providing additional memory. Microcomputer circuit 32 is coupled by data communication bus 48 to a digital controller/timer circuit 50. Microcomputer circuit 32 may be fabricated of custom IC devices augmented by standard RAM/ROM components.

The input/output circuit 30 contains the operating input and output analog circuits for digital controlling and timing circuits necessary for the detection of electrical signals derived from the heart, such as the cardiac electrogram (EGM), output from sensors (not shown) connected to the leads 14 and 15, as well as for the application of stimulating pulses to the heart to control its rate as a function thereof under the control of software-implemented algorithms in microcomputer circuit 32.

An antenna 52 is connected to input/output Circuit 30 for purposes of uplink/downlink telemetry through a radio frequency (RF) Transmitter/Receiver Circuit (RF TX/RX) 54. Uplink and downlink telemetry transmission of programming commands and analog and digital data between antenna 52 and an external device, such as an external programmer (not shown), can be accomplished employing any of the hardware and operating systems known in the art. A reed switch 51 is connected to input/output circuit 30 to enable the patient to trigger storage of syncope data when the patient feels fainting symptoms.

A crystal oscillator circuit 56, typically a 32,768 Hz crystal-controlled oscillator, provides main timing clock signals to digital controller/timer circuit 50. A Vref/Bias circuit 58 generates a stable voltage reference and bias currents for the analog circuits of input/output circuit 30. An ADC/multiplexer circuit (ADC/MUX) 60 digitizes analog signals and voltages to provide telemetry and a replacement time-indicating or end-of-life function (EOL). A power-on-reset circuit (POR) 62 functions to initialize the pacemaker 10 with programmed values during power-up, and reset the program values to default states upon the detection of a low battery condition or transiently in the presence of certain undesirable conditions such as unacceptably high electromagnetic interference (EMI), for example.

The operating mode and parameter value can be made programmable and are stored in the microcomputer circuit 32. Commands for controlling the timing of the sensing of sense events and delivery of atrial and ventricular pacing pulses are coupled by bus 48 to digital controller/timer circuit 50. Digital timers of digital controller/timer 30 time out the overall escape interval of the pacemaker, as well as various refractory, blanking and other timing windows for controlling the operation of the peripheral components coupled with leads 14 and 15 within input/output circuit 50.

Digital controller/timer circuit 50 is coupled to atrial and ventricular sense amplifiers (SENSE) 64 and 67, respectively, to atrial and ventricular electrogram (EGM) sense amplifiers 66 and 73, to atrial and ventricular pacing pulse generators (OUTPUT) 68 and 71, respectively, and to an impedance measurement circuit (Z-SENSE) 80.

An intracardiac pace/sense electrode 24 located near the distal end of lead 14 and positioned within the right ventricle 16 and a distally located intracardiac pace/sense electrode 22 of atrial lead 15 is positioned within the right atrium 17 are illustrated in FIG. 2. Ventricular pace/sense electrode 24 is coupled by a lead conductor of ventricular lead 14 to a connector element of the IPG 13 that is electrically connected with capacitors 26 and 74. Similarly, atrial pace/sense electrode 22 is coupled by a lead conductor of atrial lead 15 to a further connector element of the IPG 13 that is electrically connected with capacitors 75 and 77.

Capacitor 77 couples the atrial lead conductor to the output of the atrial pacing pulse generator 71 so that atrial pacing pulses generated by atrial pacing pulse generator 71 can be delivered to the atrial pace/sense electrode 22. Capacitor 74 couples the ventricular lead conductor to the output of the ventricular pacing pulse generator 68 so that ventricular pacing pulses generated by ventricular pacing pulse generator 71 can be delivered to the ventricular pace/sense electrode 24.

Capacitor 75 couples the atrial lead conductor to node 76 and the input of the atrial sense amplifier 67, the input of atrial EGM amplifier 73 and one input/output of the impedance measurement circuit 80. Capacitor 26 couples the ventricular lead conductor to the input of the ventricular sense amplifier 64, the input of ventricular EGM amplifier 66, and another input/output of the impedance measurement circuit 80. The atrial and ventricular sense amplifiers 67 and 64 amplify and process atrial and ventricular signals picked up from electrodes 22 and 24 to generate sense event signals for re-setting the escape interval and/or AV delay timers within digital controller/timer circuit 50. The EGM signals developed by atrial and ventricular EGM amplifiers 64 and 73 are used in those occasions when the IPG 13 is being interrogated by the external programmer/transceiver (not shown) in order to uplink telemetry transmit a representation of the analog atrial and ventricular EGM to analyze the electrical heart activity.

The impedance measurement circuit 80 operates to continually or periodically measure impedance across the pace/sense electrodes 22 or 24 and the IPG case (or another pair of sense electrodes disposed across the patient's chest) that is modulated by inspiration and exhalation and to develop a breathing rate. As is known in the art, by applying a high frequency AC carrier signal between a pair of electrodes disposed about the heart or subcutaneously implanted across the chest, e.g., pace/sense electrodes 22 and 24, a current flows through blood and lungs. Blood is more conductive than air. As volume in the lungs changes it has a large impact on measured impedance. Demodulation and processing can reveal respiratory parameters from the impedance vs. time signal, as described for example, in U.S. Pat. No. 5,318,597. Respiration parameters including respiration rate (RR) in breaths per minute, tidal volume (TV) in liters, and minute ventilation (MV), that is the product of TV and RR, can be derived from the aforementioned respiratory component of the impedance vs. time waveform. Minute ventilation can function as a rate control parameter for a rate adaptive pacemaker because it is a parameter that varies directly with hemodynamic demand.

For ease of understanding, the timing operations of the pacemaker 10 are described primarily in terms of comparisons of "rates". However, it should be understood that the intervals between successive and sequences of heart beats are actually stored and processed, and that therefore comparison of rates is actually accomplished in the device software by comparison of stored intervals. The "rate" referred to in the following description is the reciprocal of the interval separating a current heartbeat from an immediately preceding heartbeat. Thus, the vasovagal syncope detection algorithm performed by software and firmware in the microcomputer circuit 32 and digital controller/timer circuit 50 processes the intervals associated with successive heart beats, keeping a record of a preceding series of such intervals.

Figure 3:
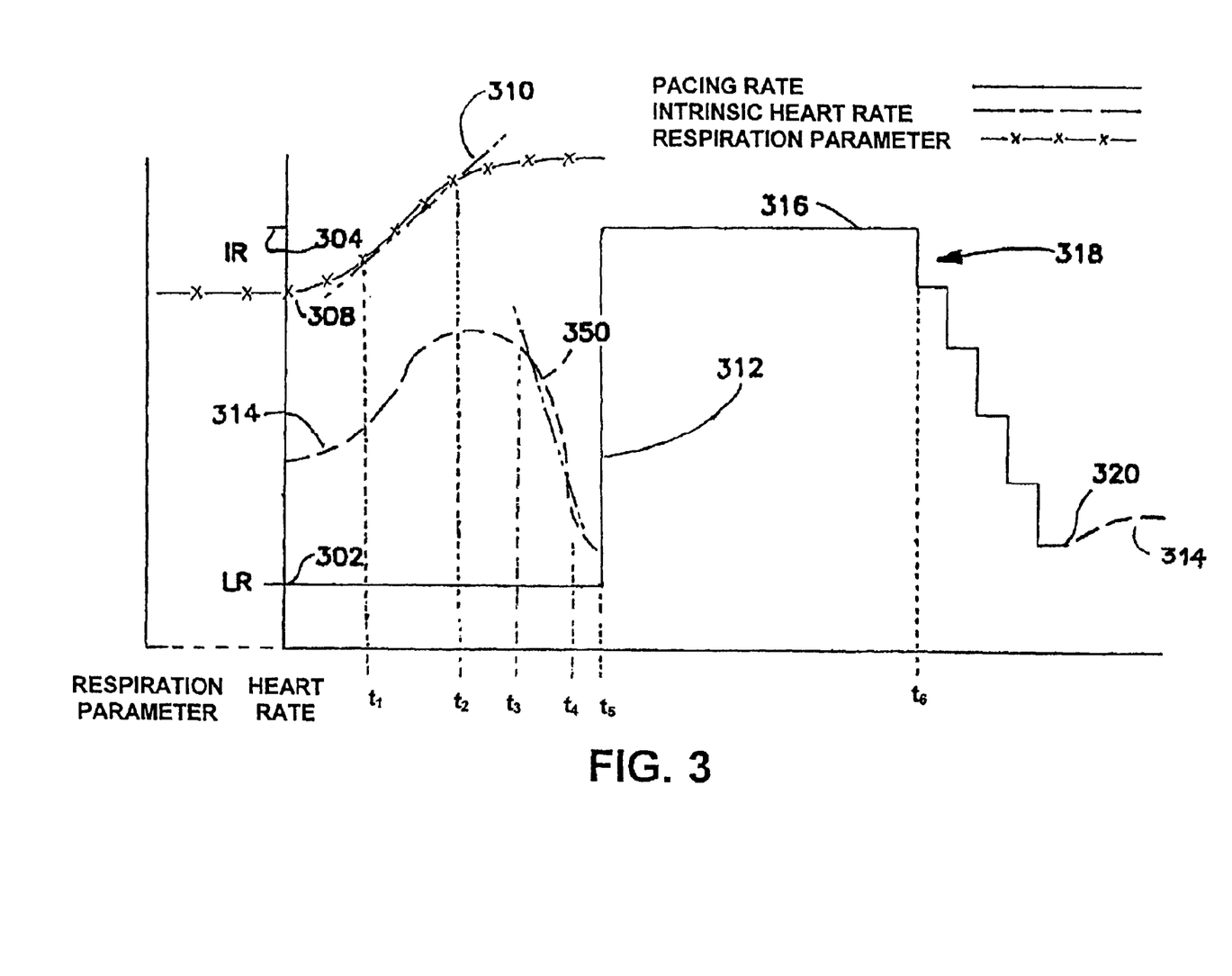
FIG. 3 is a graph of heart rate, respiration rate and pacing rate versus time illustrating the vasovagal syncope detection function and pacing intervention of the present invention.

Details of the vasovagal syncope detection feature of the present invention follow below, with reference to FIGS. 3 and 4A–4B. In FIG. 3, a pacing lower rate (LR) 302 is shown, that is the a rate below which the intrinsic heart rate HR will not be allowed to fall (also known as the base escape rate or the base pacing rate of the pacemaker). For example, this lower rate may be 50–70 beats per minute. A syncope pacing intervention rate (IR) 304 that is substantially above the lower rate is also defined. The values of these rates are programmable by the physician, and it is anticipated that the intervention rate IR should be less than or equal to the upper pacing rate limit of the pacemaker, in the case of rate-responsive or dual chamber (e.g. DDD or VDD) pacemakers.

In FIG. 3, the intrinsic heart rate (defined as the reciprocal of the interval separating the current beat from the previous beat) is illustrated as a broken line 314 and the pacing rate is illustrated by solid line 302, 312, 316, 318, 320. If the invention is practiced in a single chamber pacemaker (e.g. VVI or AAI), the pacemaker will be inhibited from delivering pulses when the patient's intrinsic heart rate 314 is higher than the pacing rate illustrated at LR 302 in FIG. 3. If the pacemaker is an atrial synchronized, dual chamber pacemaker (e.g. DDD or VDD), the pacemaker will pace the ventricles synchronized to the patient's intrinsic atrial heart rate as long as the patient's intrinsic atrial heart rate is higher than the LR 302 and if intrinsic ventricular depolarizations do not follow atrial depolarizations within a defined AV delay interval. For simplicity, it is assumed that the pacemaker is not set to a rate responsive mode, and therefore that the pacemaker's escape rate is equal to a fixed LR 302.

The LR 302 of a single or dual chamber and/or rate adaptive pacemaker implanted in patients primarily to treat occasional syncopal episodes is programmed low so that the intrinsic heart rate prevails to inhibit atrial pacing. The intrinsic heart rate and blood pressure tend to fall rapidly from a stable and regular prevailing intrinsic heart rate and blood pressure when a patient experiences syncopal episodes. The heart rate 314 does not necessarily fall below the LR 302, and so pacing at LR 302 does not normally occur before the patient experiences symptoms. In practice, it is recommended that physicians program the LR 302 to about 45–50 bpm in pacemakers implanted in patients that experience syncope.

The syncope detection algorithm of the present invention processes the heart rate HR as well as the aforementioned respiration parameters, e.g., respiration rate RR and/or tidal volume TV. The respiration rate RR and tidal volume TV can increase somewhat leading or coincidentally with or lagging with a decline in heart rate HR. In accordance with a preferred embodiment of the present invention, the prevailing or current heart rate threshold is adjusted or varied with changes in the respiration rate RR and/or tidal volume TV.

In FIG. 3, for example, an increase in the respiration parameter occurs between times $t_1$ and $t_2$, and the slope 310 of the change is determined as described below. One syncope detection criterion is satisfied, if the slope 310 exceeds a threshold slope. The satisfaction of the respiration parameter aspect, causes the heart rate threshold slope to be adjusted as set forth in FIGS. 4A and 4B described below.

The preferred particular way of assessing HR is set forth in the algorithm FIGS. 4A and 4B described below. The algorithm detects a significant, rapid heart rate drop by calculating the slope of the rate of change. An exemplary determination of the heart rate slope 350 is made in FIG. 3 between times $t_3$ and $t_4$.

In accordance with the algorithm of the present invention, the HR drop threshold or HR threshold is defined in terms of a linear regression of the heart rate HR that is continually developed from a series of heart beats occurring in a constantly updated HR window. The HR threshold is itself determined as a function of the respiration rate RR and/or tidal volume TV.

If the detected HR is below the then prevailing HR slope threshold, syncope episode data storage, uplink telemetry transmission, or therapeutic intervention is triggered in the case of a therapy delivery IMD. In this preferred embodiment, a syncope cardiac pacing therapy is delivered over an intervention time (IT) between times $t_5$ and $t_6$. Increasing the pacing rate from LR 302 to the intervention rate IR 304, at 316 in FIG. 3, provides the therapeutic intervention. The escape rate remains at the intervention rate IR for a programmed period of time or intervention time (IT) and thereafter gradually declines at 318. The syncope therapy pacing rate declines until the spontaneous intrinsic heart rate exceeds the pacing rate at 320, at which point the pacing rate is reset to the lower rate LR 302. The intervention therapy is terminated earlier if the patient's intrinsic heart rate HR spontaneously increases and exceeds the intervention rate IR. A more detailed description of an exemplary therapeutic intervention is set forth in the above-referenced '728 patent.

Figure 4A:
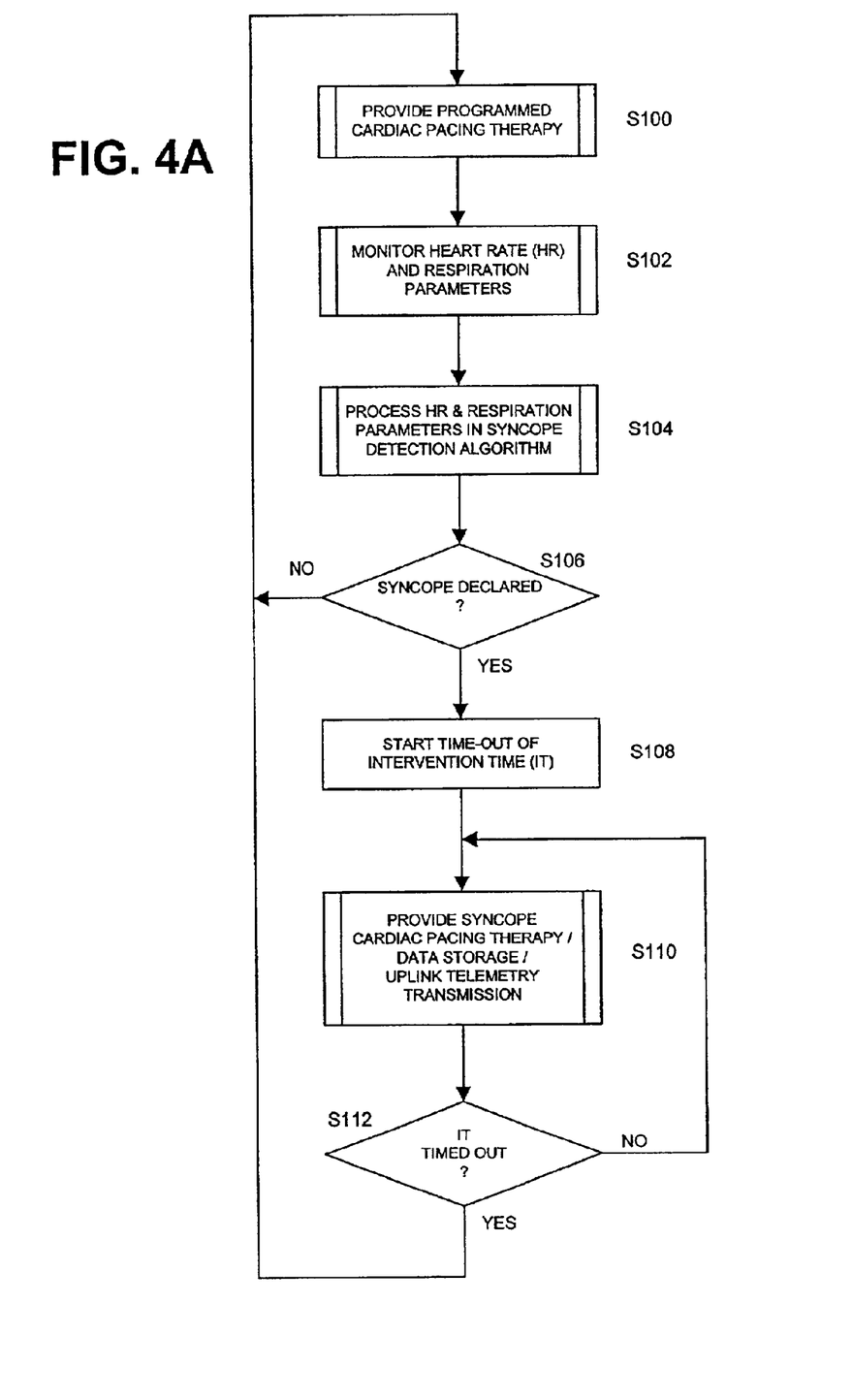
FIGS. 4A and 4B comprise a flowchart illustrating the operation of an implantable syncope pacing system embodying the invention.
Figure 4B:
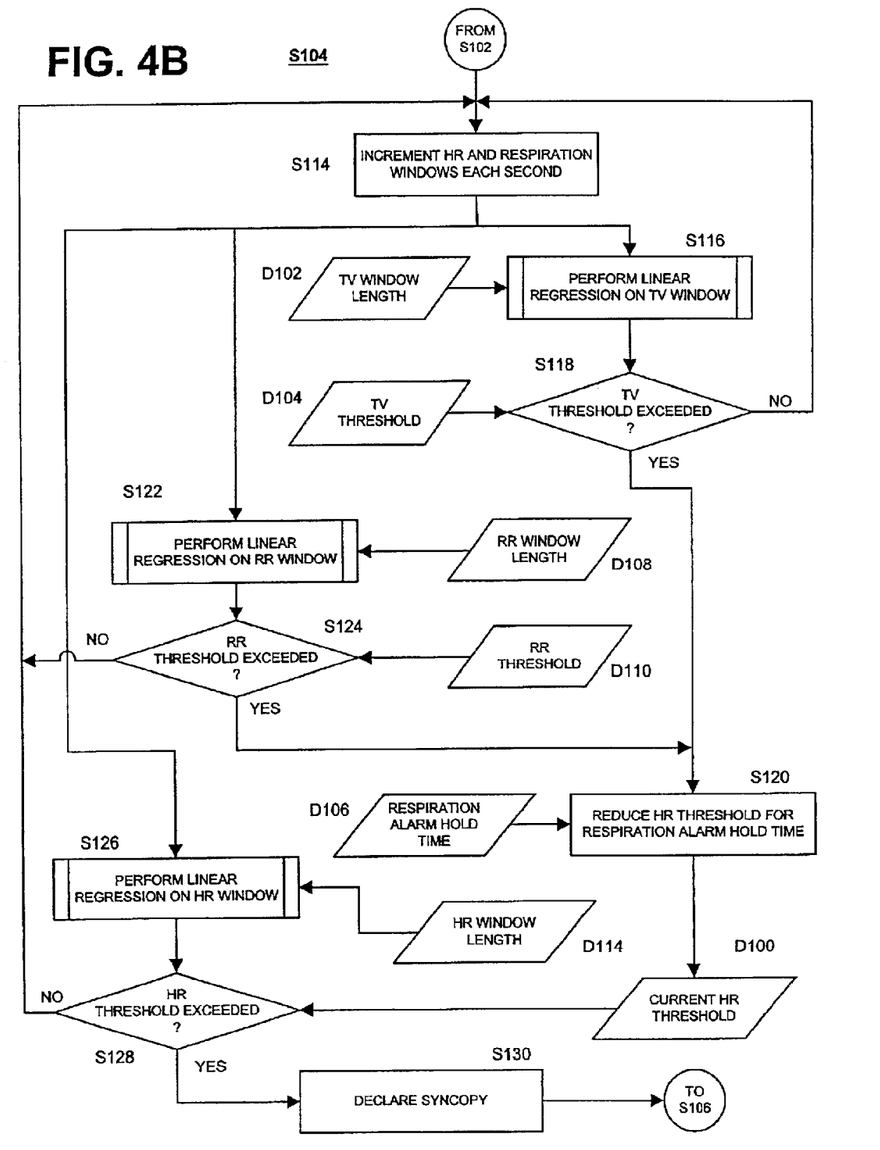

FIGS. 4A and 4B depict a preferred embodiment of the syncope detection algorithm of the present invention that triggers delivery of a syncope pacing intervention therapy when syncope detection criteria are satisfied. In FIG. 4A, the programmed cardiac pacing therapy is delivered (or monitoring takes place in a monitor IMD) in accordance with the programmed operating modes and parameter values of the pacemaker in step S100. The atrial and/or ventricular heart rate as well as the respiration parameters are continually monitored in step S102 in the manner described above with respect to the pacing system of FIG. 2 and processed in step S104 while the normal pacing therapy is delivered in step S100. The processing in step S104 can result in syncope being declared present as determined in step S106. If syncope is declared present, then an intervention time IT timer is started in step S108, and the therapy delivery and/or data storage or uplink telemetry transmission is commenced in step S110. The therapy delivery and/or data storage or uplink telemetry transmission continues for no longer than until the IT time times out as determined in step S112.

FIG. 4B illustrates one exemplary algorithm for performing step S104 of FIG. 4A wherein the heart rate HR threshold is set as a function of either the respiration rate RR or the tidal volume TV. In general terms, the HR threshold that is stored as data D100 is a relatively high or difficult threshold to meet when the rate of change of the respiration rate RR does not meet a RR rate of change or slope threshold indicative of syncope (data D110) or the tidal volume TV does not meet a TV rate of change or slope threshold indicative of syncope (data D104). But, the HR threshold in data D100 is lowered or made easier to meet if the rate of change of the respiration rate RR does meet the RR threshold rate of change indicative of syncope (data D110) or the tidal volume TV does meet the TV threshold rate of change indicative of syncope (data D104).

It will be understood that either the respiration rate RR or the tidal volume TV criteria can be employed to in a variation of the algorithm. In a further variation, both the determination of a change of the respiration rate RR that meets a RR threshold rate of change or slope indicative of syncope (data D110) and a tidal volume TV that meets a TV rate of change or slope threshold indicative of syncope (data D104) are necessary to reduce the HR threshold. In a still further variation, minute ventilation MV (the product of TV and RR) can be derived and compared to a MV threshold, and the HR threshold can be changed or reduced to reflect changes in MV.

In any of these cases, step S104 illustrated in FIG. 4B derives the current HR threshold in steps S116–S124, compares the measured HR drop or rate of change developed in step S126 to the current HR threshold in step S128, and declares a syncopal episode or syncope in step S130 if the HR threshold is exceeded. As described above with respect to FIG. 3, the HR threshold is a rate of change or a drop in heart rate.

Starting at step S114, the heart rate HR, respiration rate RR and/or tidal volume TV are continually developed and updated in step S114 and stored in respective HR, RR and TV time windows. The HR, RR and TV time windows thus hold data values that are updated on a FIFO basis and are sufficiently long for the algorithm to be able to recognize a change in HR, RR and TV that is indicative of syncope. The HR time window can be 17 seconds or so, and the RR and TV time windows can be 40 seconds or so, and both time windows can be made programmable for selection by the physician for any given patient. The processing of the data in each of the HR, RR and TV windows take place simultaneously in real time and in parallel and is updated each second, for example.

Figure 6:
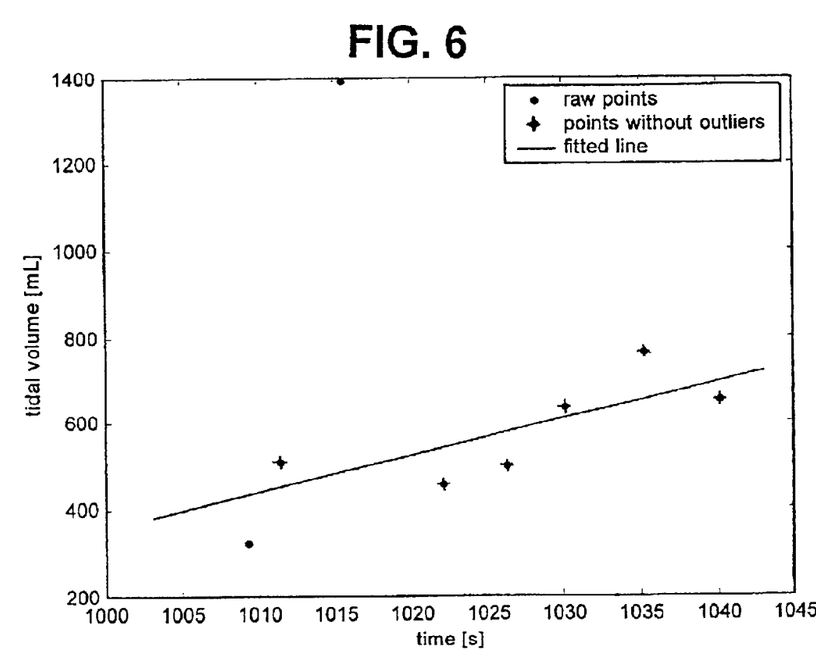
FIG. 6 is a graphical depiction of a linear regression derivation of the slope of a respiration parameter at onset of syncope.

A linear regression is performed in step S116 on the TV data in the TV data window D102 having a predetermined window length to develop a current TV slope or rate of change. An exemplary chart showing the fitted line slope of the TV data points is depicted in FIG. 6. The current TV slope or rate of change is compared to a stored TV threshold slope or rate of change in TV threshold data D104 in step S118.

A linear regression can be performed on the RR data points in step S122 on the RR data in the RR data window D108 having a predetermined window length to develop a current RR slope or rate of change. The current RR slope or rate of change is compared to a stored RR threshold slope or rate of change in RR threshold data D110 in step S124.

Figure 5:
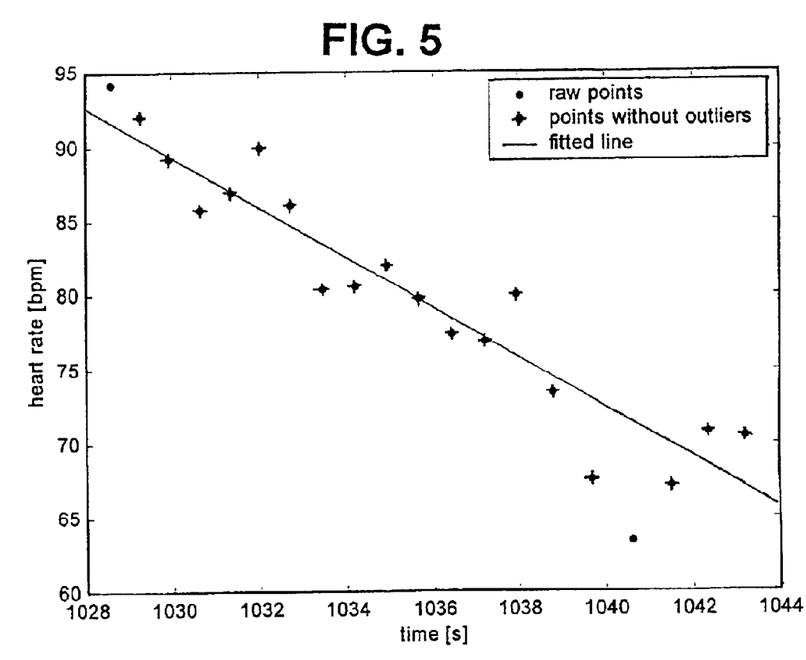
FIG. 5 is a graphical depiction of a linear regression derivation of the slope of the intrinsic heart rate at onset of syncope.

At the same time, a linear regression is performed in step S126 on the HR data in the HR data window D114 having a predetermined window length to develop a current HR slope or rate of change as shown, for example, by the fitted line in FIG. 5. The current HR slope or rate of change is compared to a stored HR threshold slope or rate of change in HR threshold data D100 in step S128.

The current HR threshold slope or rate of change in HR threshold data D100 is relatively high as long as the TV threshold criteria are not met in step S118 or the RR threshold criteria are not met in step S124. The current HR threshold slope or rate of change in HR threshold data D100 is reduced in step S120 if the TV threshold criteria is met in step S118 or if the RR threshold criteria is met in step S124 or if both the TV threshold criteria is met in step S118 and if the RR threshold criteria is met in step S124. The HR threshold slope or rate of change in each case can be a programmable value stored in memory and retrieved from memory in step S120 depending on whether steps S118 and/or S124 are satisfied or not. Or, the HR threshold slope or rate of change can be calculated in each case.

As noted above, increases in the respiration rate RR and tidal volume TV can lead or lag any reduction in the current heart rate HR and can be due to exercise or emotional stress unaccompanied by a heart rate drop. Preferably, if the HR threshold slope or rate of change is reduced in any of these ways, a "respiration alarm" is declared, and the reduction is time limited by a respiration alarm hold time of data D106. The respiration alarm hold time can be on the order of 30–40 seconds, for example.

In this way, when the present invention is incorporated into a pacing therapy delivery system or pacemaker of the type depicted in FIGS. 1 and 2, for example, pacing following a first prescribed syncope therapy rate format is initiated for a prescribed syncope pacing time when the above-described respiration parameter(s) satisfies threshold respiration criteria heart rate HR drops below the HR threshold slope or rate of change. Optionally, pacing following a second prescribed syncope therapy rate format is initiated for a prescribed syncope pacing time when a persistent or stable heart rate HR drops below the HR threshold slope or rate of change, but the patient's respiration parameters do not satisfy the from respiration criteria.

As noted above, when the present invention is incorporated into an implantable monitor, respiration rate, tidal volume and heart rate associated with a declared syncopal episode can directly uplink telemetry transmitted in real time automatically or when initiated by the patient or can be stored in IMD memory with a date and time stamp and uplink telemetry transmitted during a telemetry transmission to an external medical device to assess the patient's condition. Storage or transmission can be initiated when the patient's respiration parameter increases from a prior prevailing slope by a predetermined rate increment or to a threshold slope and heart rate drops below a threshold slope or just when the persistent or stable heart rate drops below a threshold slope.

Variations and modifications to the present invention are possible given the above disclosure. However, such variations and modifications are intended to be within the scope of the invention claimed by this letters patent. For example, although the preferred embodiment is directed to detection and treatment with respect to vasovagal syncope, the present invention can also be used with respect to neurogenic syncope, vasodepressor and cardioinhibitory disorders, such as carotid sinus syndrome.

All patents and publications referenced herein are hereby incorporated by reference in their entireties.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. An implantable medical device adapted to be implanted in a patient for detecting and declaring syncopal episodes comprising:

means for detecting a respiration parameter of the patient;

means for detecting heartbeats and for producing sense event signals related thereto;

heart rate determining means for determining a current heart rate based upon the intervals between successive sense event signals;

means for selecting a threshold heart rate drop as a function of the detected respiration parameter of the patient; and heart rate drop sensing means for sensing a drop in intrinsic heart rate from the average heart rate that exceeds the threshold heart rate drop and declaring a syncopal episode.

2. The implantable medical device of claim 1, wherein the respiration parameter comprises respiration rate and the function of the detected respiration parameter comprises an increase in respiration rate exceeding a respiration rate of change threshold.

3. The implantable medical device of claim 1, wherein the respiration parameter comprises tidal volume and the function of the detected respiration parameter comprises an increase in tidal volume exceeding a tidal volume rate of change threshold.

4. An implantable medical device adapted to be implanted in a patient for detecting and treating syncopal episodes comprising:

means for detecting a respiration parameter of the patient;

means for detecting heartbeats and for producing sense event signals related thereto;

heart rate determining means for determining a current heart rate based upon the intervals between successive sense event signals;

means for selecting a threshold heart rate drop as a function of the detected respiration parameter of the patient;

heart rate drop sensing means for sensing a drop in intrinsic heart rate from the average heart rate that exceeds the threshold heart rate drop and declaring a syncopal episode; and therapy delivery means responsive to the declared syncopal episode for delivering a therapy to counter the syncopal episode.

5. The implantable medical device of claim 4, wherein the respiration parameter comprises respiration rate and the function of the detected respiration parameter comprises an increase in respiration rate exceeding a respiration rate of change threshold.

6. The implantable medical device of claim 4, wherein the respiration parameter comprises tidal volume and the function of the detected respiration parameter comprises an increase in tidal volume exceeding a tidal volume rate of change threshold.

7. The implantable medical device of claim 4 wherein the therapy delivery means comprises pacing therapy providing means for providing a pacing therapy to the patient's heart responsive to the declared syncopal episode.

8. The implantable medical device of claim 7, wherein the pacing therapy providing means comprises pacing pulse generator means for generating cardiac pacing pulses at a predetermined differential rate in excess of an average heart rate value existing prior to declaration of a syncopal episode.

9. The implantable medical device of claim 7, wherein the pacing therapy providing means comprises pacing pulse generator means for generating cardiac pacing at a lower rate when intrinsic heart beats are not present, and for generating cardiac pacing pulses upon declaration of a syncopal episode at a predetermined differential rate in excess of the lower rate.

10. The implantable medical device of claim 7, wherein the pacing therapy providing means comprises pacing pulse generator means for generating cardiac pacing pulses at a predetermined differential rate in excess of an average heart rate value existing prior to declaration of a syncopal episode.

11. A method of operating an implantable medical device adapted to be implanted in a patient for detecting and declaring syncopal episodes comprising:

detecting a respiration parameter of the patient;

detecting heartbeats and for producing sense event signals related thereto;

determining a current heart rate based upon the intervals between successive sense event signals;

selecting a threshold heart rate drop as a function of the detected respiration parameter of the patient; and sensing a drop in intrinsic heart rate from the average heart rate that exceeds the threshold heart rate drop and declaring a syncopal episode.

12. The method of claim 11, wherein the respiration parameter comprises respiration rate and the function of the detected respiration parameter comprises an increase in respiration rate exceeding a respiration rate of change threshold.

13. The method of claim 11, wherein the respiration parameter comprises tidal volume and the function of the detected respiration parameter comprises an increase in tidal volume exceeding a tidal volume rate of change threshold.

14. A method of operating an implantable medical device adapted to be implanted in a patient for detecting and treating syncopal episodes comprising:

detecting a respiration parameter of the patient;

detecting heartbeats and for producing sense event signals related thereto;

determining a current heart rate based upon the intervals between successive sense event signals;

selecting a threshold heart rate drop as a function of the detected respiration parameter of the patient;

sensing means for sensing a drop in intrinsic heart rate from the average heart rate that exceeds the threshold heart rate drop and declaring a syncopal episode; and delivering a therapy to counter the syncopal episode.

15. The method of claim 14, wherein the respiration parameter comprises respiration rate and the function of the detected respiration parameter comprises an increase in respiration rate exceeding a respiration rate of change threshold.

16. The method of claim 14, wherein the respiration parameter comprises tidal volume and the function of the detected respiration parameter comprises an increase in tidal volume exceeding a tidal volume rate of change threshold.

17. The method of claim 14, wherein the therapy delivery step comprises providing a pacing therapy to the patient's heart responsive to the declared syncopal episode.

18. The method of claim 17, wherein the pacing therapy delivery step comprises generating cardiac pacing pulses at a predetermined differential rate in excess of an average heart rate value existing prior to declaration of a syncopal episode.

19. The method of claim 17, wherein the therapy delivery step comprises generating cardiac pacing at a lower rate when intrinsic heart beats are not present, and generating cardiac pacing pulses upon declaration of a syncopal episode at a predetermined differential rate in excess of the lower rate.

20. The method of claim 17, wherein the therapy delivery step comprises generating cardiac pacing pulses at a predetermined differential rate in excess of an average heart rate value existing prior to declaration of a syncopal episode.

* * * * *